United States Patent [19]
Slautterback

[11] Patent Number: 6,146,348
[45] Date of Patent: Nov. 14, 2000

[54] THUMB WRIST SPLINT AND METHOD

[75] Inventor: E. G. Slautterback, Coral Springs, Fla.

[73] Assignee: FLA Orthopedics, Inc., Miramar, Fla.

[21] Appl. No.: 09/317,596

[22] Filed: May 24, 1999

[51] Int. Cl.$^7$ ...................................................... A61F 5/00
[52] U.S. Cl. .................................. 602/21; 602/5; 602/6; 602/7
[58] Field of Search ............................................. 602/21

[56] References Cited

U.S. PATENT DOCUMENTS 4,716,892    1/1988    Brunswick ................................ 128/77

OTHER PUBLICATIONS

"Thumb Guide", Fla Orthopedics, Inc., Brochure No. B5–025161.

*Primary Examiner*—Richard J. Apley
*Assistant Examiner*—Jayne Saydah
*Attorney, Agent, or Firm*—Jack E. Dominik

[57] ABSTRACT

A thumb wrist splint with a main body portion which includes a plurality of straps for encircling the wrist and securing the same firmly to the wrist with desirable palmar and dorsal stays. A sewn thumb spica/splint is fabricated, and finished by normal binding around the periphery. The thumb strap loop is fixed to the splint and a removable securable anchor is also applied to the spica/splint. The spica/splint is a VOLARA® grade polyolefin closed foam material which is desirably laminated to nylon cloth on one side. The sewn thumb spica is secured to the main body portion. Thereafter, the entire blank, as just described, is positioned over an anvil intended to form a curvilinear pattern to the thus encapsulated VOLARA® so that it will conform to the upper portion of the wrist. Once secured in place on the wrist by means of the straps around the wrist portion, the thumb strap is secured. A web is applied for assistance to convert the entire splint into a sock like configuration into which the wrist and hand are inserted. The method contemplates heat softening the blank and thereafter positioning the same over an Anvil or male mold, and pressure engaging the upper portion with a mating female mold which will cause the VOLARA® to take on the shape of the male/female mold relationship and reshape to a new form.

7 Claims, 6 Drawing Sheets

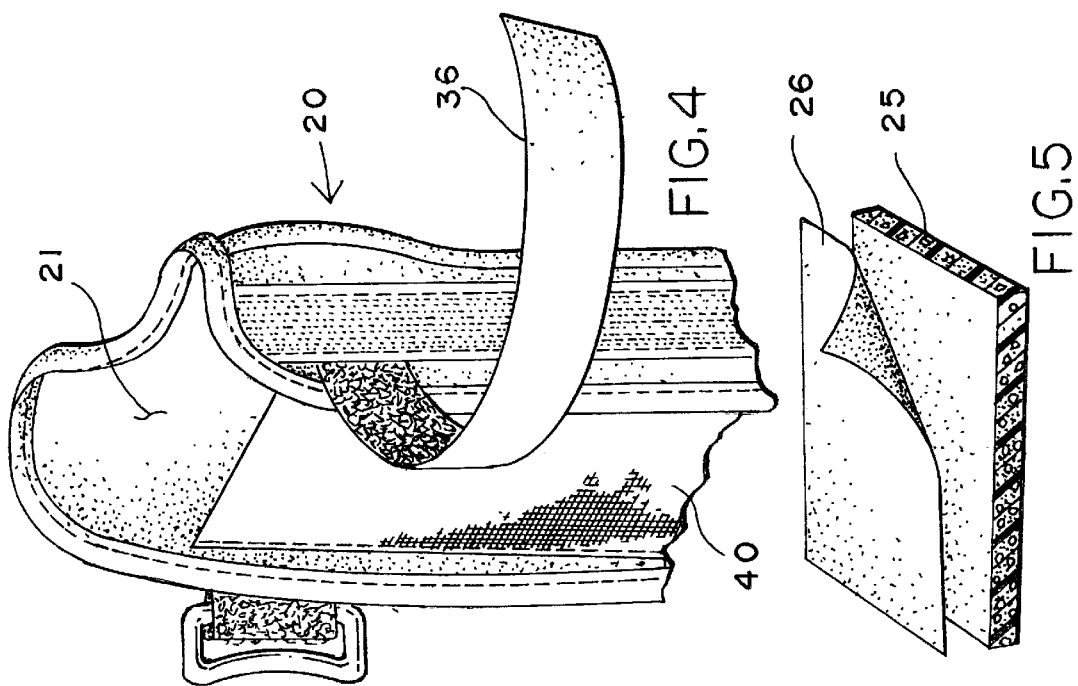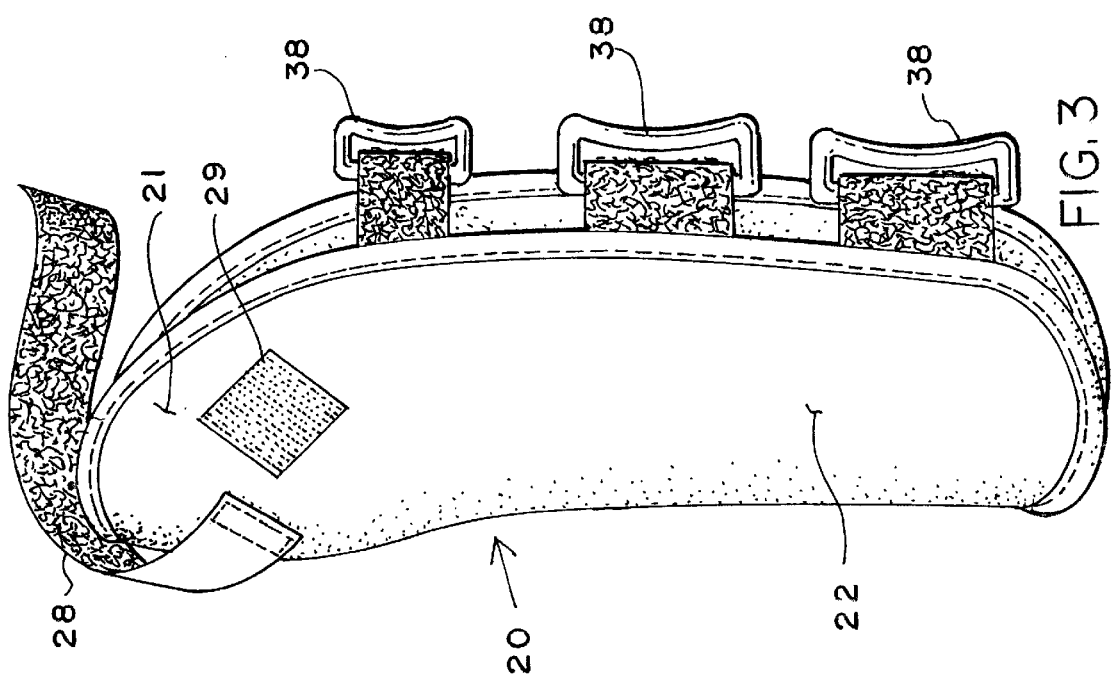

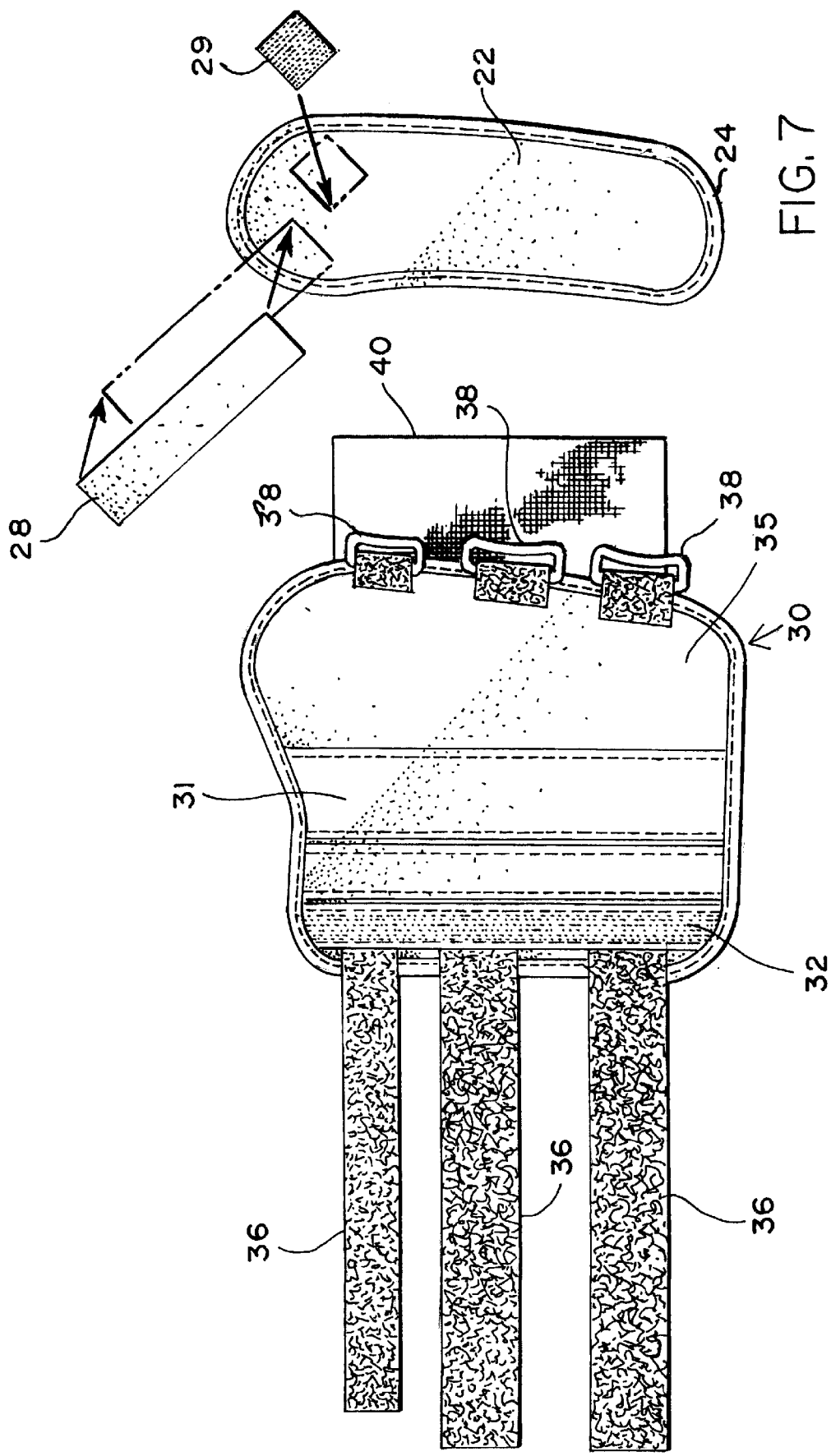

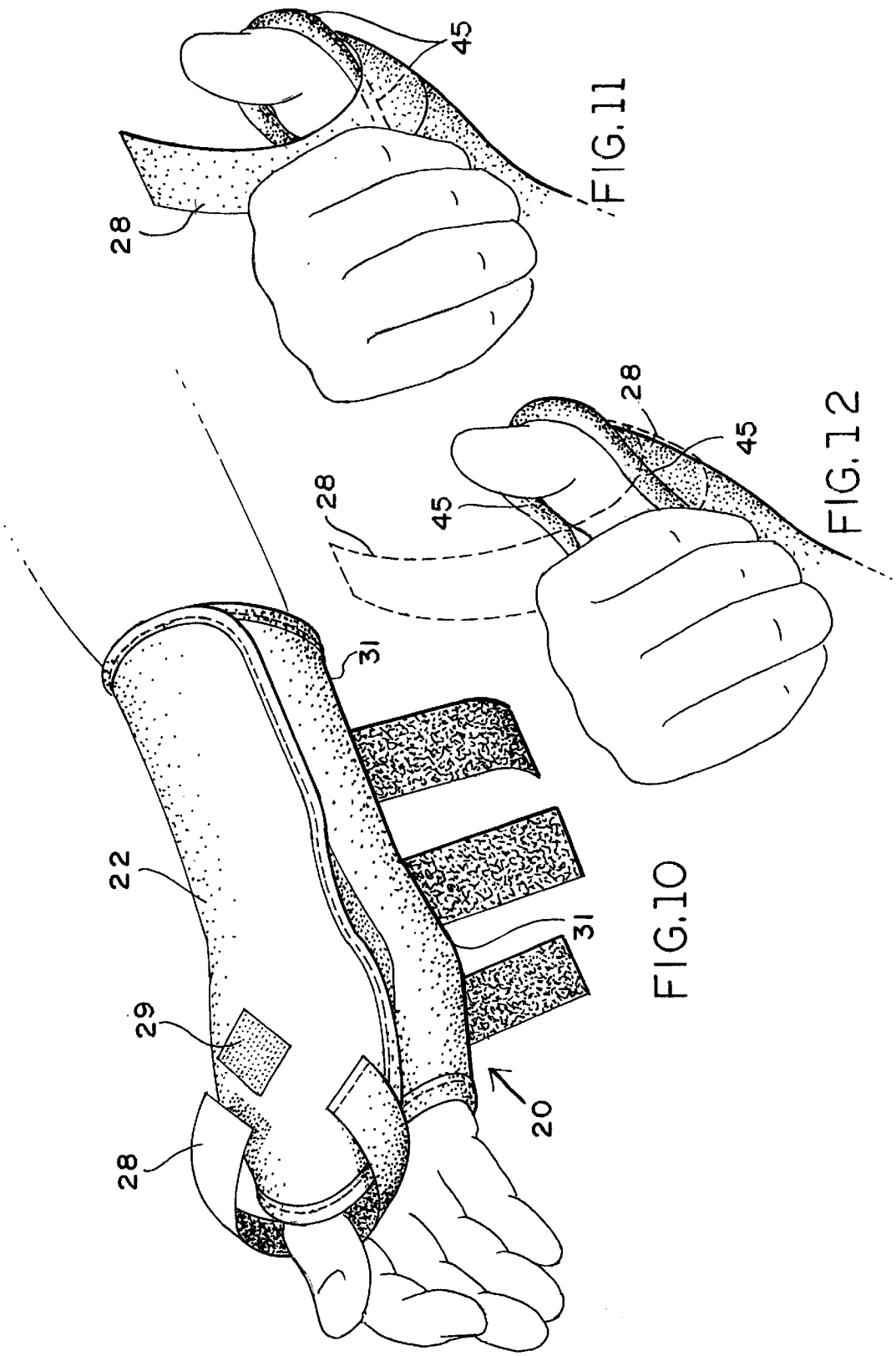

THUMB WRIST SPLINT AND METHOD

FIELD OF THE INVENTION

The present invention is directed to orthopedic products, and more particularly to a splint which is secured around the wrist with an extension portion for the thumb, often identified as a "wrist splint with thumb spica" or a "wrist splint with abducted thumb".

BACKGROUND OF THE INVENTION

Orthopedic supplies for addressing problems with the thumb are known. A "thumb guide" published by the Assignee of the subject Application is exemplary of the prior art. This "thumb guide" (Brochure B5-025161) is made of record in this Application through the concurrent filing of an Information Disclosure Statement and PTO Form-1449. More specifically it is the Applicant's product, as exemplified by Models No. 25-160 Series; 25-170002 and 25-120003.

The subject products are known as sewn orthopedic soft appliances and braces. The only means to obtain the rigidity necessary to stabilize the injured joint is by using metal or plastic straps referred to as "stays". The stays are actually sewn into the product identified in FIG. 1 of the drawings as Prior Art 1. To be noted is the abducted hand piece at the top portion which is shown in reverse appearance as in Prior Art 2. In Prior Art 1 it will be seen that there is a stay which is positioned, curved and secured by webbing.

More particularly, as shown in Prior Art 2, internal binding and internal seams are positioned around a thumb engaging portion of the splint. While the stay as shown is acceptable, it leaves something to be desired since the subject stay does not easily conform to the patient to give all the necessary support and immobilization. Moreover, some stays may be too rigid, and are too uncomfortable, or even worse will "dig" into the skin.

While low temperature formable plastic closed-cell polyolefin are known and have been used as splinting materials in a number of orthopedic products, they have not been readily used in sewn orthopedic soft appliances of the type discussed. The particular material involved is known by the Trademark VOLARA®. VOLARA® foam is formable through a variety of techniques at temperatures normally not exceeding 200° F. In addition, the product can be stitched or sewn with traditional yarns or threads.

In addressing the problem of the patient, the best immobilization of the wrist is obtained by immobilizing both the wrist and the thumb. By stabilizing the dorsal and palmar aspects of the wrist, flexion, extension, and rotation of the radius and ulnar is prevented. This type of stabilization is typically achieved with traditional wrist splints with palmar and dorsal stays. By immobilizing the Metacarpophalangeal (MCP) and basal joints of the thumb, the carpal bones of the wrist are held stable and radial/ulnar deviations are limited. This type of stabilization is typically achieved with traditional thumb spicas. The best and complete immobilization of the wrist can be obtained by combining a wrist splint with a thumb spica. This type of product is especially beneficial in post-surgical treatment of wrist and thumb injuries. However, and in addition, the same can be used to address treatment of the Basal Joint Arthritis; DeQuervain's Tenosynovitis; tendonitis; cumulative trauma disorders of the thumb and wrist; severe wrist sprains; strains/sprains of the thumb joint (MCP); wrist sprains in the Carpal region; advanced Carpal Tunnel Syndrome; or after cast removal for severe wrist fractures. Historically, wrist splints with abducted thumb pieces have been employed in these applications. To be noted, again referencing both Prior Art drawings, the abducted thumb piece is constructed with metal stays and does not conform comfortably to provide adequate immobilization with a cradle like effect on the thumb.

SUMMARY OF THE INVENTION

The present thumb wrist splint begins with the formation of the main body portion which includes a plurality of straps for encircling the wrist and securing the same firmly to the wrist with desirable palmar and dorsal stays. Thereafter, the sewn thumb spica/splint is fabricated, and finished by normal binding around the periphery. The thumb strap loop is fixed to the splint and a removable securable anchor is also applied to the spica/splint. The spica/splint is a VOLARA® grade polyolefin closed foam material which is desirably laminated to nylon cloth on one side. Thereafter, the sewn thumb spica is secured to the main body portion. At this point the product is flat and has no particular configuration. Thereafter, the entire blank, as just described, is positioned over an anvil intended to form a curvilinear pattern to the thus encapsulated VOLARA® so that it will conform to the lower forearm, wrist and thumb. Once secured in place on the wrist by means of the straps around the wrist portion, the thumb strap is secured. All of the above are desirably assisted by a web applied for assistance to convert the entire splint into a sock like configuration into which the wrist and hand are inserted. Thereafter, as suggested, the wrist straps are snugly secured and desirably reversely folded and removably secured to anchor portions, followed by wrapping elastic loop thumb strap. The elastic web, and the elastic loop thumb strap, are normally expandable by at least 20% to 40%. The method of the product further contemplates heating the blank as formed and recited above, and thereafter positioning the same over an Anvil or male mold, and thereatop pressure engaging the upper portion with a mating female mold which will cause the VOLARA® to take on the shape of the male/female mold relationship and reshape to a new form. In this process, that portion of the removed end of the thumb spica is provided with pinch points which assist in further cradling the thumb when the entire splint has been secured to the wrist and the thumb of the patient.

In view of the foregoing it is a principle object of the present invention to provide a combination of a wrist splint with a contoured thumb spica piece which ensures the practical immobilization of the wrist and thumb without interior seams and other obstructions that can irritate the skin and which are assisted by a formed angled splint.

Yet another object of the present invention is to provide such a thumb wrist splint in which the injured thumb MCP joint and/or Carpal joint of the wrist are shielded from further impact or shock. The cushioning of the VOLARA® foam provides a much better shield from such shock than a metal or plastic stay along the medial side of the wrist and hand. This results in a more comforting fit, provides a layer of foam protection, and eliminates the use of rigid metal around the sensitive MCP and Carpal joints.

Moreover, the subject product is simple and easy to sew because of the size and shape of the thumb opening. Internal stitch seams, joints and bindings, such as shown in the prior art drawing, are unavoidable due to the difficult construction of the prior art splints. Such stitch seams, as in the prior art, form pressure points that can be uncomfortable and cause aggravating pain to the sensitive joints. With the present invention such internal seams are eliminated. The entire spica portion is secured to the main body portion without seams, binding, or joints around the thumb. That renders the thumb completely and comfortably immobilized and affords protection in an unabrasive environment.

Yet another object of the present invention is to provide a thumb wrist splint which is easy to put on without third party assistance to the patient; the same result being achieved by the wrist web which gives a sock like appearance to the product when the hand of the patient is inserted therein.

Yet another object of the present invention is to achieve all of the above objects and advantages with a construction method that is inherently economical to manufacture, and in which the hand stitching and other steps are minimized.

DESCRIPTION OF ILLUSTRATIVE DRAWINGS

Further object and advantages of the present invention will become apparent as the following description of an illustrative embodiment takes place in which the accompanying drawings are as follows:

FIG. 3 is a view comparable to FIG. 1 but showing the splint of an illustrative embodiment of the present invention with the thumb spica portion at the top, the thumb strap at the top, and the laminated VOLARA® foam over the wrist with the interior webbing.

FIG. 4 is the inside view shown in FIG. 3 partially broken at the lower portion to illustrate the abducted thumb spica portion without stitching, binding, seams, or other interruptions.

FIG. 5 is an exploded partial cut-away view of the VOLARA® foam and the nylon cloth which is applied to one face thereof.

FIG. 6 illustrates the main body portion and the interior pad in plan view.

FIG. 7 shows the edge bound VOLARA® pad ready for thumb strap and thumb strap anchor attachment.

FIG. 10 is a partial perspective view of the illustrative thumb wrist splint showing the right hand of the patient.

FIGS. 11 and 12 are sequential views showing how the pinch point formed in the VOLARA® pad portion of the splint engages the thumb, particularly after the thumb strap is secured in place.

DESCRIPTION OF ILLUSTRATIVE EMBODIMENT

Figure 2:
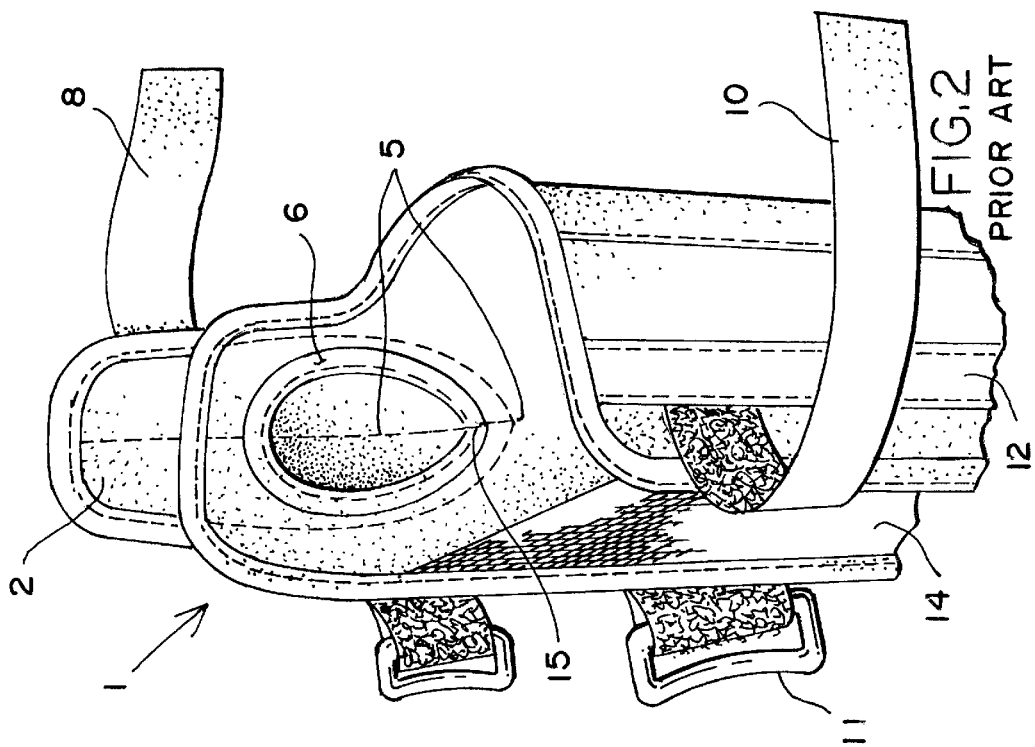
FIG. 2 is a rear view of the prior art shown in FIG. 1 illustrating the abducted hand piece at the top, the internal binding and internal stitching inside the unit.
Figure 1:
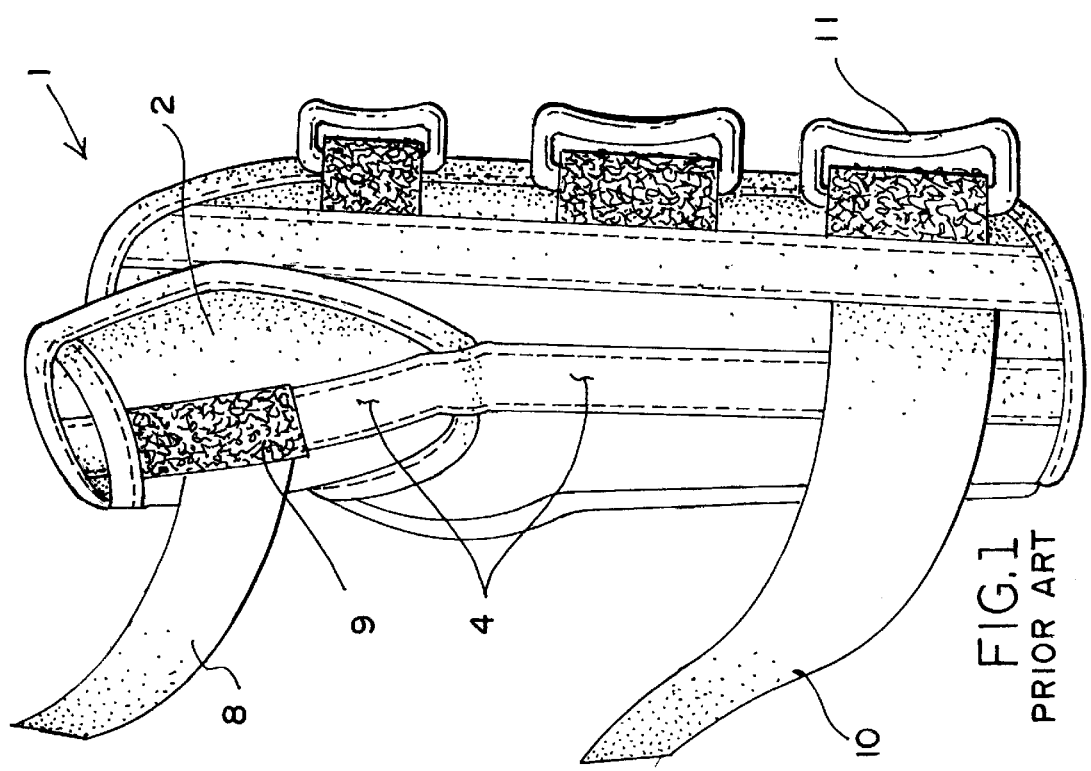
FIG. 1 is a view of the prior art assembled thumb angle splint showing the stay curved with the webbing on the thumb side of the unit, and abducted hand pieces at the top.

The present invention will become even more apparent when taken in the context of the prior art as illustrated in FIGS. 1 and 2. FIG. 1 shows the prior art splint 1 with an abducted thumb piece 2. To be noted is the stay secured with webbing 4 and, as seen in FIG. 2, a plurality of internal seams 5, and internal binding 6. At the upper portion a thumb strap 8 (expandable) is wrapped around the thumb and secured to the thumb strap anchor 9 to secure the thumb in place.

A plurality of wrist straps 10 with opposed anchors 12 secure the wrist strap after it passed through the wrist buckles 11. Once secured in place, with the assistance of the wrist webbing 14, the internal bindings 6, internal seams 5, and internal joint 15 can all bind on the wrist and thumb base of the user. This is an invitation for discomfort depending upon the quality of workmanship in making the splint, as well as the configuration of the thumb and wrist of the patient. The present invention, to be described hereinafter, is addressed to an uninterrupted thumb and thumb base engagement area in combination with a formed plurality of splints which immobilize and yet comfortably secure, particularly when engaged with pinch points around the thumb.

Turning now to FIG. 3, it will be seen that the thumb wrist splint 20 with its upper thumb spica portion 21, have a significant portion which is formed of a laminated VOLARA® foam wrist and thumb spica pad 22. This material can be obtained through the VOLTECH Division of SEKISUI American Corporation located in Lawrence, Mass. 01843. To be noted in the upper portion of FIG. 4, the interior area, there are not internal bindings, seams, or joints. The wrist webbing 40 is a mesh material and assists in applying the thumb wrist splint by converting it into the form of a sleeve into which the hand, thumb, and forearm are inserted.

In FIG. 5 there is an exploded view of the VOLARA® foam wrist and thumb spica pad 22. It shows a laminated nylon cloth 26 which is secured to one surface of the VOLARA® foam 25. This portion of the spica pad 22 is shaped by a unique process, as will be discussed hereinafter.

Turning now to FIG. 6, there is shown the interior pad 30 which will be ultimately formed into the thumb wrist splint 20. The internal pad 30 includes a palmar stay 31 which is curved to fit the inner wrist and the palm of the hand. In addition, provision is made for a dorsal stay 32. However, the stays 31 and 32 are relatively inflexible and hard. Conversely, the thumb spica base 35 receives the VOLARA® foam wrist and thumb spica pad 22, as shown in exploded form to the right of the interior pad 30. It will be noted that binding 24 has been applied to the VOLARA® foam wrist and thumb spica pad 22. At a convenient phase of the manufacturing, the thumb strap 28 is applied to the VOLARA® foam wrist and thumb spica pad 22 as shown in diagrammatically in FIG. 7, and then the thumb strap anchor 29 is also applied to the VOLARA® foam wrist strap and thumb spica 22. As shown in both FIGS. 6 and 7, the basic components are flat.

Figure 8:
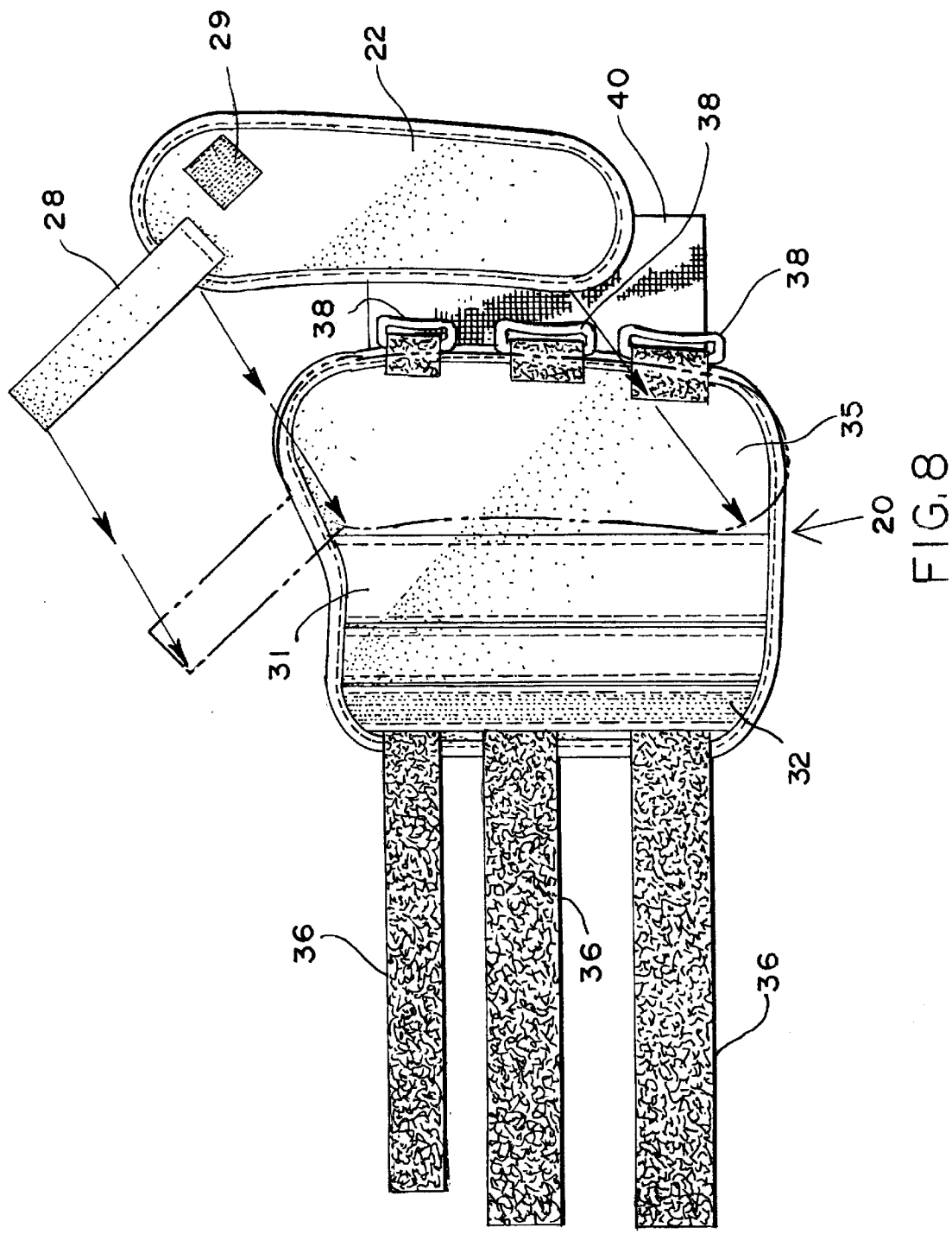
FIG. 8 illustrates the same entity as shown in FIGS. 5, 6 and 7 but in its immediate exploded relationship to the VOLARA® thumb spica.

Turning now to FIG. 8, it will be seen that the VOLARA® foam wrist and thumb spica pad is translated into position over the wrist and thumb spica base 35 and then desirably stitched into place. Once stitched into place, the thumb strap 28 and thumb strap anchor 29 are also in position to carry out their designated functions. In addition, it will be seen that there are a plurality of wrist straps 36 provided and dimensioned to reversely fold through the wrist strap buckles 38 and then the wrist webbing 40 is secured in place to provide a sleeve like member.

Figure 9:
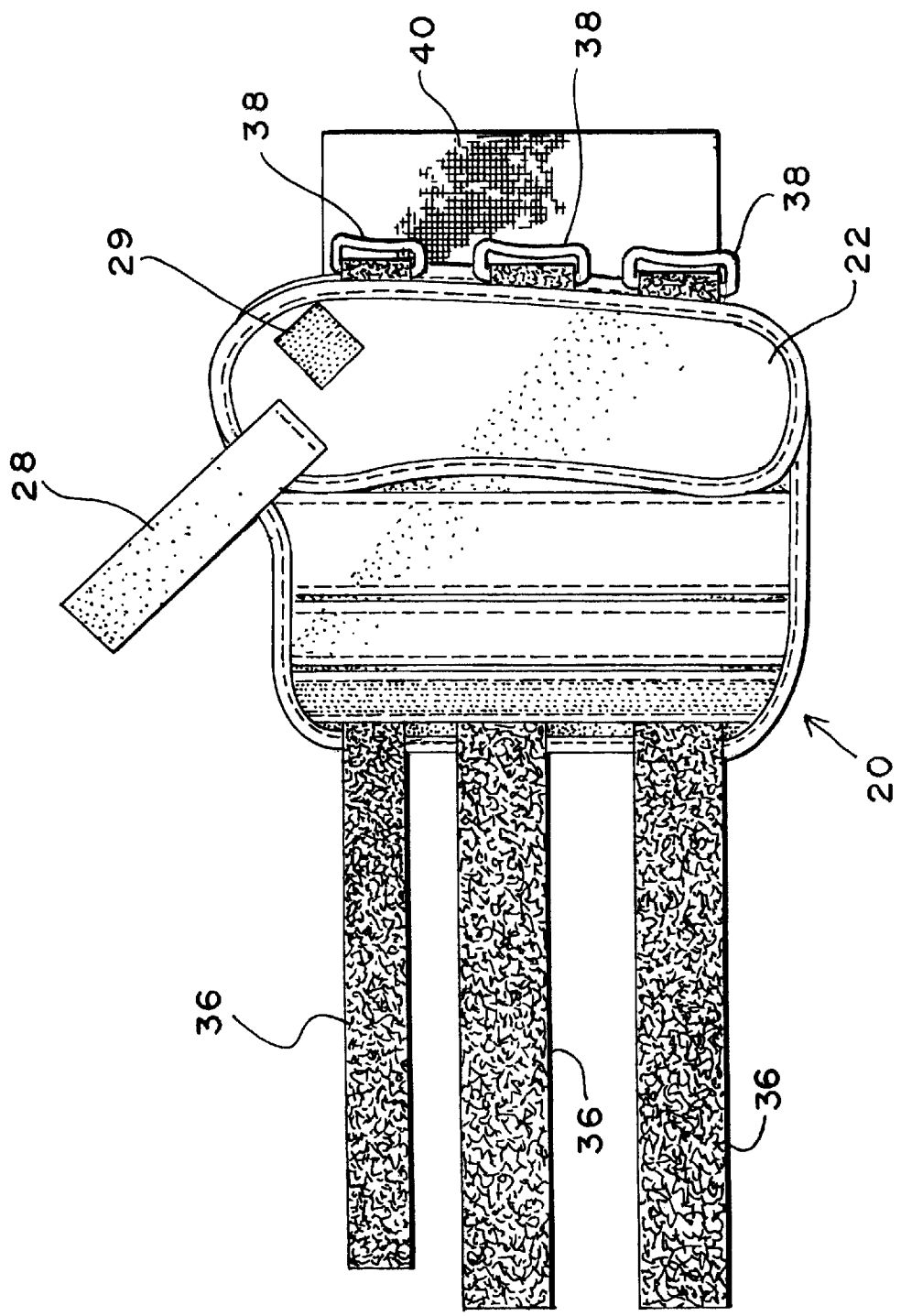
FIG. 9 is a plan view showing the spica in place over the basic underbody of the main portion of the wrist splint, subsequently sewn thereto, and ready for forming.

Finally, as shown in FIG. 9 the entire assembly is completed with the exception of sewing the wrist webbing 40 in place, and forming the VOLARA® foam wrist and thumb spica pad 22 into a configuration where it will overlie the inner portion of the wrist and base of the thumb extending upwardly in the thumb spica as best shown in FIG. 10.

The forming of the VOLARA® foam wrist and thumb spica pad 22 in its assembled relationship is done by placing the same over an anvil which imparts the male portion of the shape. However, prior to placing over the anvil the entire unit is heated, normally with a plurality of such units, in an oven to a temperature not to exceed 200° F. Once that temperature is achieved, one by one the assemblies can be positioned over the anvil male member, and thereafter a clamping female member is pressed downwardly on the unit to impart the shape, as desirably shown in FIG. 10. The shaping members, both the anvil and the clamp, are cooled at all times by blowing chilled air over the same, or by internal piping of a recirculatory cold water to cool the same and cause the VOLARA® foam wrist and thumb spica pad 22 to take its final shape.

In addition, as shown particularly in the sequence of FIGS. 11 and 12, pinch points 45 are formed in the VOLARA® at the top of the thumb spica base 35 to further cradle the thumb, particularly as shown in FIG. 12.

It will be understood that various changes in the details, materials and arrangements of parts, or method which have been herein described and illustrated in order to explain the nature of the invention, may be made by those skilled in the art within the principle and scope of the invention as expressed in the appended claims.

What is claimed is:

1. A thumb wrist splint comprising, in combination, an interior pad having opposed lateral edge portions;

said interior pad having a curved palmar stay secured in a mid portion thereof;

a plurality of wrist straps extending laterally from the interior pad;

a plurality of wrist strap receiving members at an opposed position on the interior pad for removably securing the wrist straps;

a thumb spica portion extending from an upper portion of the interior pad;

said thumb spica portion having secured to it a wrist and thumb spica pad formed from a polyolefin closed foam material which is formable at a temperature up to 200° F.;

a thumb strap secured to an upper portion of said wrist and thumb spica pad;

means for removably securing said thumb strap to the wrist and thumb spica pad;

said interior pad and spica pad being formed to develop a curvilinearly opposed thumb spica portion;

whereby a thumb wrist splint is developed which has a fixed palmar stay for engaging the upper portion of the forearm, and a thumb spica portion for snugly engaging the thumb which is formed from the formable material of the spica pad.

2. In the thumb wrist splint according to claim 1, a web member secured to one lateral edge of the interior pad, and also secured to the opposite edge of the interior pad;

thereby giving the entire thumb wrist splint a sleeve like configuration to facilitate securement to the forearm by the patient without assistance from an outsider.

3. In the thumb wrist splint according to claim 1, a pair of opposed pinch points on the interior portion of the thumb spica;

whereby the thumb is more securely anchored interiorly of the spica by pinch points which engage the thumb in a segment of curvilinear material exceeding 180° around the thumb.

4. In the thumb wrist spica of claim 1, said means for securing the end of said wrist straps comprising a plurality of elongate buckle type members secured to the interior pad at one lateral edge of the interior pad;

whereby the wrist straps are inserted into said buckle type members for removable securement.

5. In the thumb wrist splint of claim 4, a wrist webbing removably securable member overlying the dorsal stay.

6. In the thumb wrist splint of claim 1, said foam wrist and thumb spica pad having a cloth portion laminated thereto;

said cloth portion being secured interiorly of the interior pad.

7. In the thumb wrist splint of claim 6, binding secured around the periphery of said foam wrist and thumb spica pad;

whereby there is an absence of stitching in the thumb engaging area otherwise characteristic of thumb wrist splints.

* * * * *